United States Patent [19]

Fischer

[11] Plant 5,068

[45] Jul. 12, 1983

[54] AFRICAN VIOLET NAMED SWAN LAKE

[75] Inventor: Arnold W. Fischer, Hanover, Fed. Rep. of Germany

[73] Assignee: Pan-American Plant Company, Parrish, Fla.

[21] Appl. No.: 252,316

[22] Filed: Apr. 9, 1981

[51] Int. Cl.[3] ..... A01H 5/00

[52] U.S. Cl. ..... Plt./69

[58] Field of Search ..... Plt./69

*Primary Examiner*—James R. Feyrer

*Attorney, Agent, or Firm*—Chas. W. Rummler

[57] ABSTRACT

A new and distinct African Violet cultivar characterized by its intermittent blooming habit and its profuse production of blossoms when flowering, and by its large, star-shaped, flowers which are borne in a cluster above the foliage on strong, upright stems, the flowers being particularly graced by their gently ruffled petals.

4 Drawing Figures

BACKGROUND OF THE NEW PLANT

My new African Violet cultivar originated as a seedling of unknown parentage growing among a field of African Violet plants maintained in greenhouse at Fallbrook, Calif., for breeding purposes. This new plant was discovered by me in 1977 and was selected for propagation because of its vigorous growth and beautifully colored, star-shaped blooms of large size. This new plant was reproduced by cuttings at Fallbrook and subsequently propagated through several successive generations, which demonstrated that its novel characteristics would hold true from generation to generation and appeared to be firmly fixed. This new African Violet plant is now being propagated on a commerical scale, by means of cuttings, at West Chicago, Ill., and at Parrish, Fla.

DESCRIPTION OF THE DRAWINGS

This new violet plant is illustrated by the accompanying drawings, of which sheet 1 is a photographic view of a potted plant in full bloom showing the general arrangement and display of the flowers, sheet 2 is a photographic print showing a full face view of a flower of this variety which has been hand-painted to show the true flower colors, and sheets 3 and 4 are prints of machine copies of the front and back sides, respectively, of typical leaves of this plant.

DESCRIPTION OF THE NEW PLANT

The following is a detailed description of the new plant based upon observations made in greenhouse at West Chicago, Ill., the color designations being according to The R.H.S. Colour Chart published by The Royal Horticultural Society of London, England.

THE PLANT

Origin: Seedling.
Parentage: Unknown.
Classification:
*Botanic.*—*Saintpaulia ionantha.*
*Commercial.*—African Violet potted plant.
Form: Compact and of rosette shape.
Growth: Vigorous and strong.
Growth rate: Rapid.
Foliage:
*Number of leaves.*—About 13.

*Size of leaf.*—Length — From insignificant to about 100 mm. Width — From insignificant to about 90 mm.
*Shape.*—Ovate with obtuse tip, cordate base, and repand margin.
*Texture.*—Pubescent.
*Aspect.*—Glossy.
*Color.*—Upper side — 137A. Under side — 138D.
*Ribs and veins.*—Pinnate and very prominent on under side of leaf.
*Leaflets.*—None.
*Petioles.*—Length — About 22 to 82 mm.

THE BUD

Form: Vase-shaped.
Size: Average with various lengths and diameters at time of opening.
Opening rate: Typical violet.
Color of petals:
*When sepals first divide and petals begin to unfurl.*—77C.
Sepals:
*Number.*—Five.
*Shape.*—Lanceolate and branched, becoming flat when flowers open.
*Color.*—Inside — 148B. Outside — 199B.
*Striae.*—None.
Calyx:
*Size.*—Small.
*Shape.*—Calyx splits to star shape.
*Aspect.*—Hairy.
Peduncle:
*Length.*—From insignificant to about 84 mm.
*Aspect.*—Hairy.
*Strength.*—Erect and rigid.
*Color.*—199C.

THE FLOWER

Blooming habit: Intermittent.
Flowering: Profusely.
Flower size: Large.
*Diameter.*—About 35 to 45 mm.
*Borne.*—As a cyme.
*Shape.*—When bloom first opens, cup-shaped; becoming flat when bloom matures.
Petalage:
*Number of petals.*—Five.
*Arrangement.*—Sympetalous.

*Form.*—Rotate and actinomorphic with repand and gently ruffled margins.
*Texture.*—Soft.
*Appearance.*—Satiny.
*Color.*—Top side — 77B.
Petaloids: None.
Flower stem:
*Length.*—From insignificant to about 84 mm.
*Character.*—Strong and upright.
*Color.*—199C.
Discoloration: After full bloom, the color fades to 77C.
Persistence: The flowers hang on and dry.
Fragrance: None.
Lasting quality:
*On the plant.*—10 to 20 days when fully opened.

REPRODUCTIVE ORGANS

Stamens:
*Anthers.*—Number: Two. Arrangement: Monadelphous. Size: About 3 mm. square. Color: Yellow.

*Filaments.*—Length: About 4 mm. Color: Whitish yellow.
*Pollen.*—Color — Yellow.
Pistils:
*Number.*—One.
*Styles.*—Length: About 6 mm. Color: 77C.
*Stigma.*—Color — Whitish.
Ovaries: Hypogynous and tomentose.

This new variety of African Violet plant is particularly distinguished by its profusion of blooms borne on stems of various lengths in a bouquet above the medium green foliage of the rosette shaped plant, the actinomorphic, deep pink flowers being star-shaped, of medium size and having excellent keeping quality.

I claim:

1. A new variety of African Violet plant, substantially as herein shown and described, characterized by its profuse production of large, deep pink flowers borne on upright stems to cluster above the plant foliage.

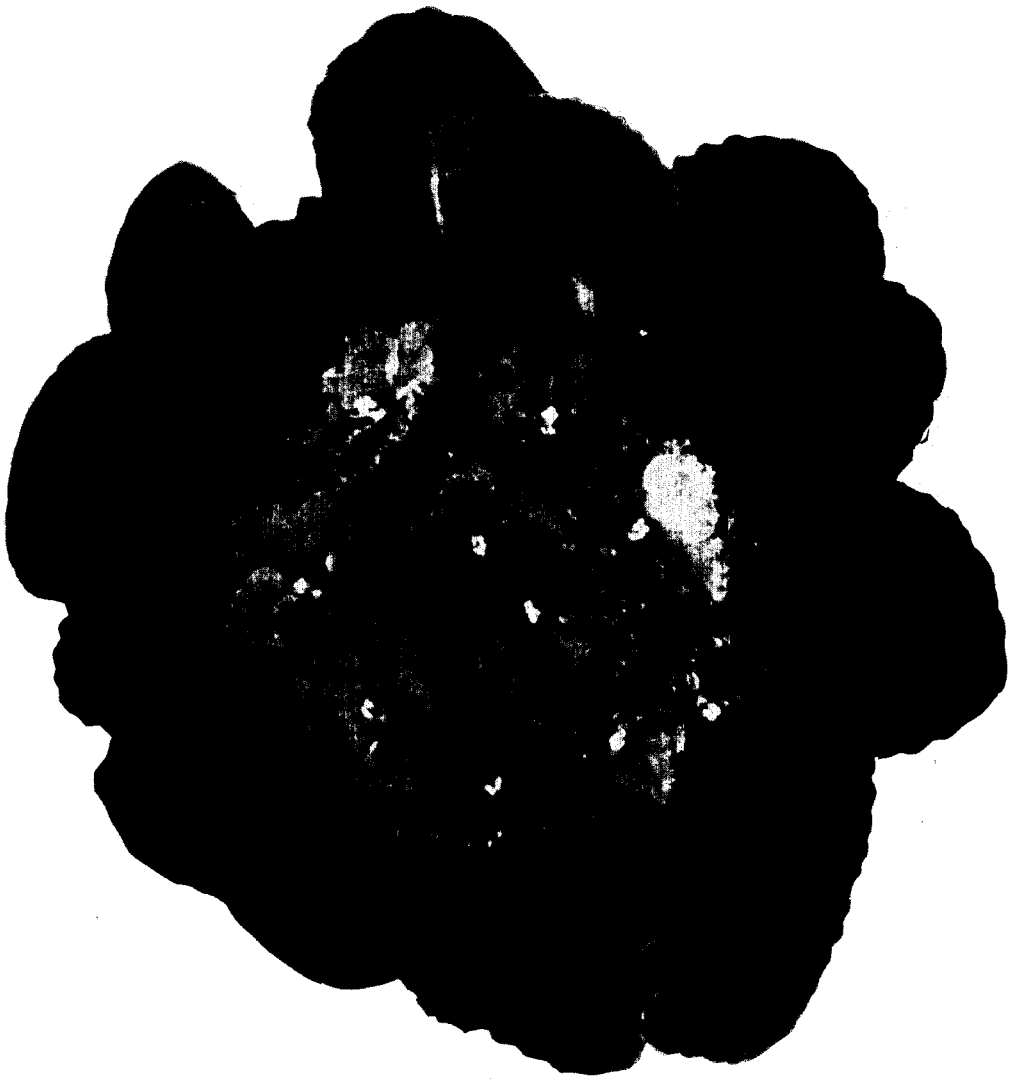

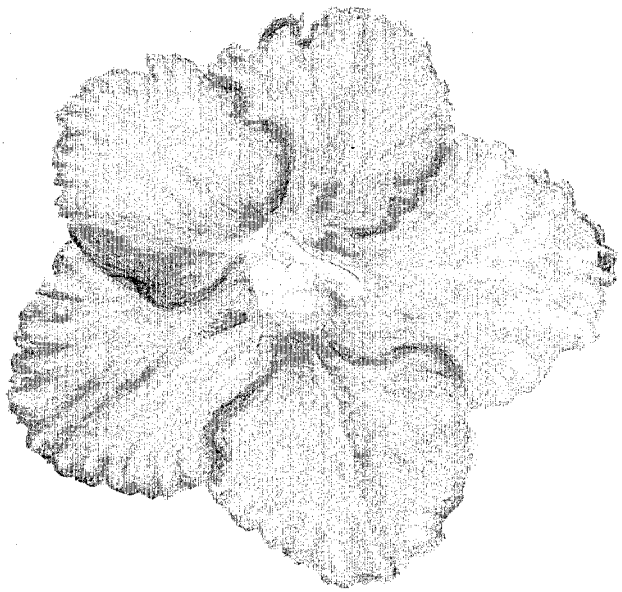

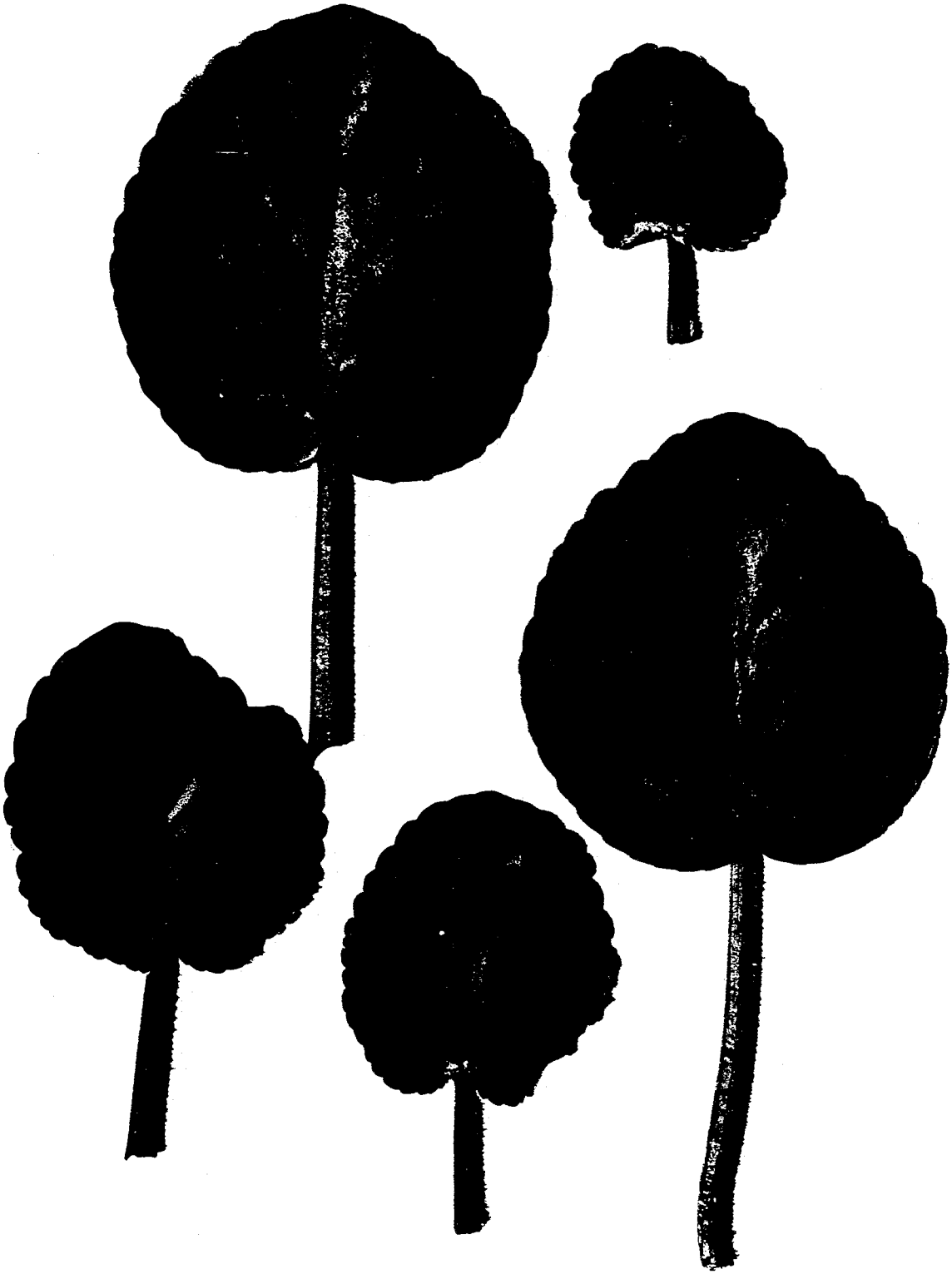

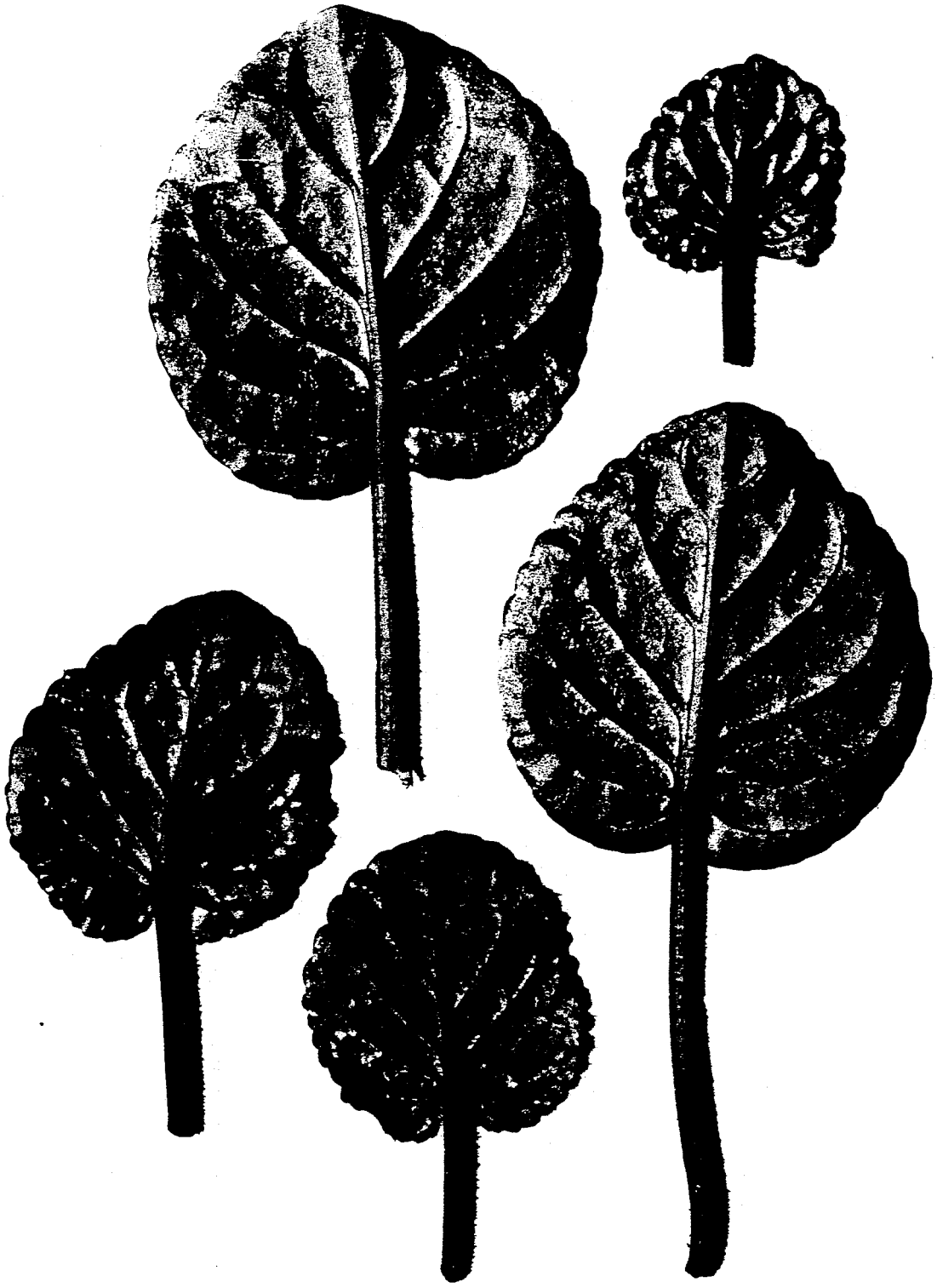

* * * * *